(12) United States Patent
Peyman

(10) Patent No.: US 7,722,581 B2
(45) Date of Patent: May 25, 2010

(54) CRYSTALLINE LENS DRUG DELIVERY

(75) Inventor: Gholam A. Peyman, 8654 Pontchartrain Blvd. Unit #1, New Orleans, LA (US) 70124

(73) Assignee: Gholam A. Peyman, Tucson, AZ (US)

(*) Notice: Subject to any disclaimer, the term of this patent is extended or adjusted under 35 U.S.C. 154(b) by 279 days.

(21) Appl. No.: 11/103,283

(22) Filed: Apr. 11, 2005

(65) Prior Publication Data
US 2006/0225745 A1 Oct. 12, 2006

(51) Int. Cl.
*A61M 35/00* (2006.01)
(52) U.S. Cl. ................................ 604/289
(58) Field of Classification Search ........... 623/6.18, 623/6.21; 606/107; 604/289, 294
See application file for complete search history.

(56) References Cited

U.S. PATENT DOCUMENTS

| | | | | |
|---|---|---|---|---|
| 4,191,176 A * | 3/1980 | Spina et al. | | 604/28 |
| 5,362,478 A | 11/1994 | Desai et al. | | 424/9 |
| 5,439,686 A | 8/1995 | Desai et al. | | 424/451 |
| 5,498,421 A | 3/1996 | Grinstaff et al. | | 424/450 |
| 5,560,933 A | 10/1996 | Soon-Shiong et al. | | 424/489 |
| 5,665,382 A | 9/1997 | Grinstaff et al. | | 424/450 |
| 5,672,355 A * | 9/1997 | Refojo et al. | | 424/427 |
| 5,811,510 A | 9/1998 | Papisov | | 528/230 |
| 5,863,990 A | 1/1999 | Papisov | | 525/398 |
| 5,916,596 A | 6/1999 | Desai et al. | | 424/489 |
| 6,096,331 A | 8/2000 | Desai et al. | | 424/422 |
| 6,375,986 B1 | 4/2002 | Ryde et al. | | 424/489 |
| 6,506,405 B1 | 1/2003 | Desai et al. | | 424/450 |
| 6,528,067 B1 | 3/2003 | Magdassi et al. | | 424/264 |
| 6,537,579 B1 | 3/2003 | Desai et al. | | 424/489 |
| 6,592,903 B2 | 7/2003 | Ryde et al. | | 424/489 |
| 6,690,964 B2 * | 2/2004 | Bieger et al. | | 600/424 |
| 6,749,868 B1 | 6/2004 | Desai et al. | | 424/491 |
| 6,753,006 B1 | 6/2004 | Desai et al. | | 424/422 |
| 6,822,086 B1 | 11/2004 | Papisov | | 536/24.2 |
| 6,936,053 B1 * | 8/2005 | Weiss | | 606/107 |
| 2003/0185757 A1 | 10/2003 | Kresse et al. | | |
| 2004/0010310 A1 | 1/2004 | Peyman | | |
| 2005/0009772 A1 * | 1/2005 | Caprioli | | 514/44 |

* cited by examiner

*Primary Examiner*—Kevin C Sirmons
*Assistant Examiner*—Deanna K Hall
(74) *Attorney, Agent, or Firm*—Wenderoth, Lind & Ponack L.L.P.

(57) ABSTRACT

A method of delivering a drug or other compound to the lens of the eye. A conduit through which a drug is introduced penetrates at least the outer lens capsule for drug delivery. When withdrawn, the aperture is self-sealing, thus minimizing trauma and minimizing the risk of cataract formation. The drug remains localized within the lens.

16 Claims, 1 Drawing Sheet

CRYSTALLINE LENS DRUG DELIVERY

FIELD OF THE INVENTION

The invention is directed to a method for ocular drug delivery.

BACKGROUND

A cataract refers to any opacity of the ocular crystalline lens. The normal crystalline lens is transparent, refractive, and provides adequate accommodation (shape change) to transmit and focus light on the retina at various distances. Accommodation in the human eye occurs through controlled changes in crystalline lens shape, thickness, and refractive surface placement relative to the cornea. With cataracts, the normally clear lens becomes cloudy, affecting the transmission of light through the lens and resulting in loss of visual acuity. Cataracts are most frequently associated with the normal aging process or pathology, but injury or mechanical violation of the ocular capsule surrounding the lens also causes cataract formation.

Because of the risk of inducing cataract formation, penetrating the lens capsule to introduce drugs or other agents into the lens has not been favorably considered.

SUMMARY OF THE INVENTION

One embodiment of the invention is an ocular drug delivery method by penetrating at least the outer capsule of the lens with a fine conduit that creates a self-sealing aperture when it is removed, then introducing a drug into the lens through this aperture. For example, a 30 gauge or higher needle, connected to a syringe, can be used. In various embodiments, the agent can be introduced into any part of the lens (e.g., anterior and/or posterior portion), into more than one location in the lens, and ultrasound can be performed to visualize placement of the conduit within the lens. The drug may be in a nanotechnology formulation.

This method provides a drug or other agent(s) directly to the lens while minimizing the risk of cataract formation. It also contains the agent within the lens, so that a higher than normal concentration of drug may be effectively delivered, or gene therapy may be provided directly to the lens with less concern for systemic toxicity, untoward treatment outcomes, etc. For example, a gene or gene fragment (promoter, etc) may be delivered in a vector using the inventive method, allowing positive or negative regulation of lens epithelial cell proliferation, mortality, and/or integrity.

By regulating the depth of conduit penetration, the length of the conduit and/or by visualizing conduit placement, the agent can be delivered to the lens capsule, subcapsular epithelium, cortex, and/or nucleus.

These and other advantages will be apparent in light of the following figures, detailed description, and example.

DETAILED DESCRIPTION

The inventive method provides for the introduction of agents directly to the crystalline lens with a minimized risk of inducing cataract formation.

Figure 1:
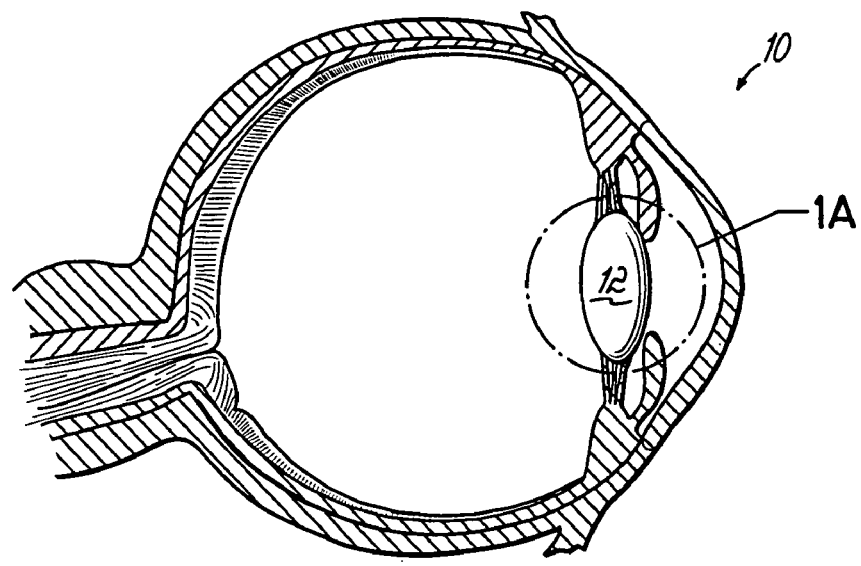
FIG. 1 illustrates a side elevational view in cross-section of a human eye.
Figure 1A:
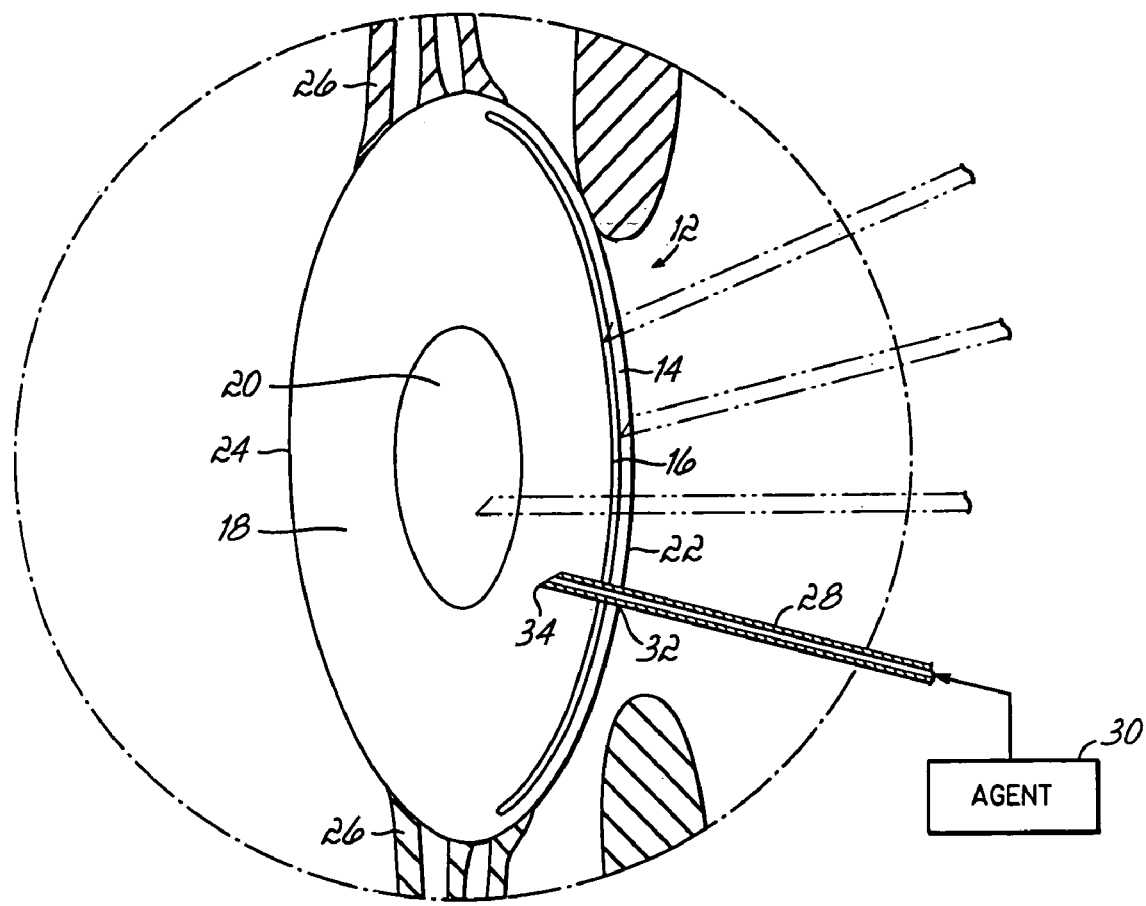
FIG. 1A is an enlarged view of the encircled area of FIG. 1 showing a conduit to introduce agents into the lens.

As shown in FIGS. 1 and 1A, the normal human eye 10 includes a transparent bioconvex crystalline lens 12, which is generally composed of four layers: the lens capsule 14, the subcapsular epithelium 16, the cortex 18, and the nucleus 20. The lens capsule 14, which includes an anterior capsule portion 22 and a posterior capsule portion 24, is a clear, membrane-like structure that encases the dense cellular elements of the lens 12. The lens capsule 14 is elastic, permitting the lens 12 to accommodate or change shape upon relaxing and contracting the zonular ligaments 26 attached to opposed ends of the lens capsule 14. The subcapsular epithelium 16 is a monolayer of epithelial cells beneath the anterior capsule portion 22 that produce lens fibers making up the lens cortex 18 and nucleus 20.

As described in more detail below, in some ophthalmologic procedures it is desirable to deliver various agents to the crystalline lens 12. This permits agents to be delivered directly to a site requiring evaluation and/or therapy. Use of a conduit to deliver agents into the lens allows the agents to be selectively located within the lens, and also allows the agents to be confined or localized within the lens. Thus, it provides a method to deliver localized therapy. As one example, an increased concentration of a therapeutic and/or diagnostic agent may be introduced directly into the lens. Because of its localization and confinement within the lens, there is less of a concern for distribution to other ocular structures or for systemic distribution with concomitant toxicity, side effects, drug-drug interaction, etc. As another example, a vector containing a therapeutic gene may be introduced directly into the lens. Because of its localization and confinement within the lens, there is less of a concern for release or dissemination of the gene, etc., beyond the site of delivery.

As illustrated in FIG. 1A, a fine conduit 28 is used to introduce agents, shown schematically at 30 in FIG. 1A, into the lens 12 with a minimized risk of inducing cataract formation. In some ophthalmologic applications, it may be necessary to precisely locate the agent 30 within one or more of the various layers of the lens 12, such as the lens capsule 14 and/or the subcapsular epithelium 16. Introduction of agents 30 includes, but is not limited to, a therapeutic gene or portion thereof, a regulatory gene or portion thereof, a gene inducer or promoter, a gene inhibitor, an oligonucleotide, gene vectors, drugs, etc., with configuration or formulation of any of the above using nanotechnology, as known to one skilled in the art.

As used herein, a conduit 28 generally refers to any structure that defines an enclosed passageway through the structure. As examples, the conduit 28 may be or may include a needle, a cannula, a tube (e.g. glass, plastic, metal) or any other structure known to one skilled in the art that includes such a passageway. In one embodiment, conduit 28 provides passage for the agents 30 into the lens 12 proper, or into a specific portion of the lens 12, via a self-sealing aperture 32 of the lens capsule 14 caused by a fine gauge portion or tip 34 of conduit 28. A fine gauge portion or tip 34 is generally of 30 gauge diameter or higher (smaller diameter), with the higher the gauge, the thinner the needle. Such a delivery system minimizes, reduces, or prevents cataract formation. While not bound to a particular theory or mechanism, the reduced size of entry minimizes trauma to the lens capsule 14.

One example of such a conduit 28 in accord with the invention is a fine gauge needle. While needle size refers to both the length and gauge (thickness) of the needle, it is the needle gauge that is sufficiently thin for use in the inventive method. In one embodiment, a needle having a 30 gauge diameter (0.31 mm outer diameter) or higher (smaller outer diameter) may be used. Needles having a high gauge diameter (e.g. a 42 gauge diameter, 0.14 mm outer diameter) are commercially available, for example, Hamilton Company (Reno Nev.); Popper and Sons, (New Hyde Park N.Y.); synergetics™, inc. (St. Louis Mo.); Alcon (Houston Tex.); Bausch & Lomb (Rochester N.Y.) and other medical supply companies. Non-limiting examples include a 39 gauge rigid microinjection cannula straight, a 42 gauge rigid microinjection cannula straight, a 39 gauge rigid microinjection cannula angled, a 42 gauge rigid microinjection cannula angled, a 39/21 gauge rigid microinjection cannula straight with a 21 gauge shaft, a 42/21 gauge rigid microinjection cannula straight with a 21 gauge shaft, a 39/21 gauge rigid microinjection cannula angled with a 21 gauge shaft, and a 42/21 gauge rigid microinjection cannula angled with a 21 gauge shaft.

Another example of such a conduit 28 is a microcapillary pipette available for intracellular/extracellular microinjection. The microcapillary pipette is generally formed from a capillary tube, which generally ranges in size between 1-2 mm outer diameter and may be made from borosilicate glass or other suitable materials such as aluminosilicate or quartz. Such capillary tubes may be obtained commercially, or may be self-manufactured, e.g., formed from glass capillary tubes. To form the microcapillary pipette, the capillary tube is held in a device (termed a pipette puller, e.g., Sutter Instrument, Novato Calif.; Tritech Research, Los Angeles Calif.) and a portion of the tube is heated to the softening point of the particular material. Once the softening point is reached, a pulling force is applied to each end of the capillary tube, thinning the tube along the softened portion so as to have a desired diameter. Depending on a number of variables, such as capillary material type, temperature, and pulling force among others, numerous types and diameter sizes may be formed. This technique may, for example, be used to produce microcapillary pipettes with tip diameters of 0.02 µm. Those of ordinary skill in the art will recognize that the microcapillary pipettes may also go through additional processing steps, such as a beveling process to the tip 34 to facilitate penetration and/or agent delivery into the lens 12.

A number of devices that contain or are capable or containing agent may be coupled to the conduit 28. In one embodiment, the conduit 28 is coupled to a standard syringe containing the agent 30. The syringe may be calibrated to indicate the volume of agent 30, facilitating accurate dosage of agent injected into the lens 12. For example, a fine gauge needle or a microcapillary pipette operatively coupled with a commercially available syringe (e.g., Hamilton Company, Reno Nev.) may be used to introduce an agent 30 into the lens 12.

In one embodiment, a patient is prepared for the procedure with a local anesthetic, which may be injected, applied topically, etc. Under an operating microscope, a physician penetrates the lens capsule 14 with the tip or end 34 of conduit 28, such as the tip of a needle or micropipette as previously described, at one or more selected lens locations to deliver the agent. The choice of site(s) depends upon a variety of factors, such as the particular ophthalmologic treatment, location of pathology, lens size (child vs. adult), physician preference, etc. For example, as shown in FIG. 1A, the tip 34 of conduit 28 may be positioned within the cortex 18. The invention, however, is not so limited, and the particular length of the conduit 28 may be selected to facilitate positioning within the nucleus 20, the subcapsular epithelium 16, or the cellular layers that make up the lens capsule 14 (shown in phantom in FIG. 1A). Moreover, the invention is not limited to penetration of the lens capsule 14 via the anterior capsule portion 22. In one embodiment, the conduit 28 may also penetrate the lens capsule 14 via the posterior capsule portion 24. In one embodiment, more than one conduit 28 may be introduced in a single procedure. Ultrasound may be used to visualize placement of tip 34 or conduit 28 within the lens.

Agent 30 is introduced into the lens 12, either directly through the tip 34 of conduit 28 or through a syringe barrel or other device coupled to conduit 28 (e.g., by manually depressing a plunger on the syringe). A conduit 28 and syringe, as described above, may be used for ophthalmologic therapies where precise positioning of the tip 34 of conduit 28 within lens 12 is not required. Alternatively, the position of the tip 34 of conduit 28 within the lens 12 may be secured by, for example, a biologically compatible sealant, adhesive, etc.

In another embodiment, a microinjection system may be used to introduce agent 30 into the lens 12 in a controlled and precise manner. Such a microinjection system generally includes a microinjector coupled to conduit 28 to finely control the amount or volume of agent 30 being dispensed through the conduit 28, and a micromanipulator to finely control the position of the tip 34. As is known in the art, different types of microinjectors are commercially available (e.g., Eppendorf AG, Hamburg, Germany; Tritech Research, Los Angeles Calif.). Microinjectors include syringe-based microinjectors, pneumatic or oil based microinjectors, and motor-driven microinjectors. The microinjectors are configured to control the amount or volume of agent 30 through the conduit 28. For example, a syringe-based microinjector generally includes a support or base, and a connecting member adapted to receive the barrel of a syringe. The end of the syringe is coupled to the conduit 28 through which the agent 30 will be dispensed. In one embodiment, a needle is coupled to the end of the syringe. In another embodiment, a micropipette is directly or indirectly coupled to the end of the syringe. The microinjector further includes an actuator that cooperates with the syringe or the plunger of the syringe such that displacement of the actuator causes the agent 30 to be dispensed through the conduit 28.

In one embodiment, the actuator is manually manipulated. To this end, the microinjector typically includes a screw with a handle or knob on one end. Movement of the knob in one direction, such as the clockwise direction, will advance the actuator toward the syringe and thereby dispense the agent 30 in the syringe through conduit 28. In a similar manner, movement of the knob in an opposite direction, such as the counterclockwise direction, will retract the actuator away from the syringe. Thus by manipulating the knob, the amount or volume of agent 30 dispensed through conduit 28 may be controlled. As those of ordinary skill in the art will recognize, the movement of the actuator may be controlled in other ways. Furthermore, those of ordinary skill in the art will recognize that pneumatic or motor driven microinjectors are available that also allow precise amounts or volumes of agent 30 to be dispensed.

The microinjection system may include a micromanipulator. The micromanipulator includes a connecting member adapted to couple to the conduit 28. The micromanipulator is configured such that the connecting member, and thus the conduit 28, may be moved in one or more directions. In one embodiment, a three-axis micromanipulator is used to control the position of the connecting member in three-dimensional space. In one aspect, the micromanipulator may be manually operated. To this end, the micromanipulator may include three handles that control movement of the connecting member along the three mutually exclusive axes. Thus, by manipulating the three handles, the position of conduit 28 may be controlled so as to accurately dispense agent 30 at a particular depth and into a particular site or location within lens 12. As those of ordinary skill in the art will recognize, the movement of the connecting member may be controlled in other ways. For example, instead of manual handles, the micromanipulator may include stepper motors that are coupled to a controller. The controller then actuates the stepper motors to move the connecting member in three-dimensional space to a desired location. The controller may include a joy stick such that movement of the joy stick in a certain direction causes movement of the connecting member in a corresponding direction. Micromanipulators of the type described above are commercially available (e.g., Eppendorf AG, Hamburg Germany; Tritech Research, Los Angeles Calif.).

In any of the above-described embodiments, the placement of tip 34 and/or delivery agent within the lens may be verified by ultrasound visualization.

In one embodiment, one or more agent(s) 30 that influences the shape of the lens 12 may be administered. Such an agent, or combination of agents 30, may be introduced at the anterior capsule portion 22 and/or the posterior capsule portion 24 to decrease or increase lens convexity. The agent(s) 30 may be injected under the lens capsule 14 or under the lens 12. These agents 30 include synthetic and/or organic materials including collagens, mucopolysaccharides, glycosaminoglycans, liquid silicon, etc.

In one embodiment, an agent 30 that minimizes or prevents lens hardening, enhances or increase lens softening, and/or returns or enhances lens plasticity and/or elasticity may be administered. As one example, an agent 30 that damages the cell membrane to enhance dissolution of lens fibers within the lens cortex 18 or the lens nucleus 20 may be administered. As another example, an agent 30 that renders the lens 12 more elastic is administered to an individual with presbyopia. As another example, an agent that reduces or prevents senescence may be administered to immortalize cells or cell types within the lens.

In one embodiment, an agent 30 that inhibits cell proliferation of the lens epithelium 16 may be administered. Such an agent 30 may reduce, delay, or prevent opacification of the anterior and/or posterior capsule portion 22, 24, respectively, after cataract surgery. As one example, a pharmacological compound and/or a vector carrying a gene modifying the survival of the lens epithelium 16, or causing it to produce compounds which enhance survival of the lens epithelium 16 or other lens fibers, may be administered. Such agents 30 may be administered alone, or in combination with antiproliferative agents to reduce capsular opacification and cell proliferation. These antiproliferative agents are known to one skilled in the art and include, but are not limited to, methotrexate, cyclophosphamide, ifosphamide, 5-fluorouracil, 5-fluorouridine, cytarabine, bleomycin, mitomycin-c, etc.

In one embodiment, one or more antioxidants are provided to the lens using the inventive method. It is known that glucose metabolism and its associated effect on redox potential have a role in crystalline lens alteration; this may induce oxidative damage. Thus, antioxidant agents (e.g., drugs with radical scavenging properties, vitamin E, vitamin C, carotenes, lutein, zeaxanthin, molybdenum, retinol, etc.) may be provided into the lens.

Any of the above agents may be formulated. Genes may be provided in vectors (e.g., entrained, targeted, encapsulated, etc.). Drugs may be formulated as nanoparticles or nanocrystals of pharmaceutically active compounds, and/or nanoscale dispersions, encapsulations, and emulsions (e.g., to limit or prevent aggregation or reaggregation of crystals, to incorporate a stabilizer, etc). The drugs may be combined with albumin or another non-toxic solvent to form nanoparticles in a solvent-free formulation of a toxic drug. The drugs may be formulated as sugar-derived nano compounds that may shield proteins and small molecules from rapid breakdown. The drugs may be rendered more soluble in a nanocrystal formulation by decreasing drug particle size and hence increasing the surface area thereby leading to increased dissolution. These techniques are known to one skilled in the art as disclosed in, for example, U.S. Pat. Nos. 6,822,086; 6,753,006; 6,749,868; 6,592,903; 6,537,579; 6,528,067; 6,506,405; 6,375,986; 6,096,331; 5,916,596; 5,863,990; 5,811,510; 5,665,382; 5,560,933; 5,498,421; 5,439,686; and 5,362,478; and U.S. patent application Ser. Nos. 10/106,117; 60/147,919; and 08/421,766, each of which is expressly incorporated by reference herein in its entirety.

The invention with be further appreciated with respect to the following non-limiting example.

EXAMPLE

A 33 gauge needle penetrated the lens capsule and epithelium of a New Zealand white rabbit. The tip of the needle was positioned within the cortex. Fluorescein dye, contained within a barrel of the syringe coupled to the needle, was injected into the lens (0.1 µl-3 µl) by manual depression of the syringe plunger.

At eight weeks post-injection, the fluorescein solution had uniformly stained the entire lens, detectable upon visual observation. This indicated that the solution had disseminated from the single site of injection throughout the entire compact dense cellular material of the lens. Moreover, at eight weeks post-injection, there was no cataract formation observed upon ophthalmologic evaluation. There was minimal scarring and no evidence of permanent egress or ingress of fluid from inside or outside the eye at the injection site.

These data supported the likelihood that an agent, such as a vector containing a therapeutic gene, when injected into the lens, will be confined to the lens. Thus, any post-injection cell proliferation that may lead to cataract formation will be minimized or reduced.

Other variations or embodiments of the invention will also be apparent to one of ordinary skill in the art from the above figures, description, and example. Thus, the forgoing embodiments are not to be construed as limiting the scope of this invention.

What is claimed is:

1. An ocular drug delivery method comprising penetrating at least an outer capsule of an ocular lens with a conduit to create an aperture in the lens and introducing a drug into the lens through the aperture, wherein the aperture is self sealing upon removal of the conduit, the method containing the drug within the lens for therapy to the lens with minimized cataract formation without removing lens material for the therapy at any time throughout the duration of the therapy after removing the conduit from the outer capsule, and wherein the drug is configured to disperse throughout the entire lens.

2. The method of claim 1 wherein the conduit is a needle have a thickness of 30 gauge or higher.

3. The method of claim 1 wherein the conduit is a needle having a thickness of 30 gauge to 42 gauge.

4. The method of claim 1 further comprising performing ultrasound to visualize placement of the conduit.

5. The method of claim 1 wherein the drug is in a nanotechnology formulation.

6. The method of claim 1 wherein the drug is an oligonucleotide.

7. The method of claim 1 wherein the drug is at least a portion of a therapeutic gene in a vector.

8. The method of claim 7 wherein the vector is a virus or a plasmid.

9. The method of claim 1 wherein the drug regulates at least one of cell proliferation, cell mortality, or cell integrity.

10. The method of claim 9 wherein regulation is inhibitory or stimulatory.

11. The method of claim 1 wherein the conduit penetrates at least one of a lens capsule, a lens subcapsular epithelium, a lens cortex, or a lens nucleus.

12. The method of claim 1 wherein the conduit penetrates an anterior lens capsule or a posterior lens capsule.

13. The method of claim 1 wherein the drug is hydrophilic or is mixed with a hydrophilic solution.

14. A localized ocular drug delivery method comprising penetrating at least an outer capsule of an ocular lens with a conduit to create an aperture, providing an agent directly into the lens via the conduit through the aperture, and withdrawing the conduit wherein the agent is substantially confined within the lens for therapy without removing lens material at any time as part of the therapy after withdrawing the conduit from the outer capsule, and wherein the agent is configured to not be removed from the lens.

15. The method of claim 14 wherein the agent is hydrophilic or is mixed with a hydrophilic solution.

16. A method that minimizes cataract formation when an agent is provided to an ocular lens, the method comprising piercing the lens with a needle of 30 gauge or thinner, introducing an agent into the lens through the needle, and withdrawing the needle from the lens, the method minimizing cataract formation without removing lens material at any time as part of the therapy after removing the needle from the lens wherein the agent is configured to disperse throughout the entire lens.

* * * * *